US006681979B2

(12) United States Patent
Whitman (10) Patent No.: US 6,681,979 B2
(45) Date of Patent: *Jan. 27, 2004

(54) FLUID DELIVERY DEVICE FOR USE WITH ANASTOMOSING STAPLING, AND RESECTING INSTRUMENTS

(75) Inventor: Michael P. Whitman, New Hope, PA (US)

(73) Assignee: Power Medical Interventions, Inc., New Hope, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/303,294

(22) Filed: Nov. 25, 2002

(65) Prior Publication Data

US 2003/0073982 A1 Apr. 17, 2003

Related U.S. Application Data

(63) Continuation of application No. 09/510,933, filed on Feb. 22, 2000, now Pat. No. 6,488,197.

(51) Int. Cl.[7] .......................... A61B 17/04; A61B 17/10
(52) U.S. Cl. ....................... 227/180.1; 604/43
(58) Field of Search .................. 227/19, 155, 179.1, 227/180.1, 867.1, 145.1; 604/43, 544; 606/153

(56) References Cited

U.S. PATENT DOCUMENTS

| | | |
|---|---|---|
| 1,881,250 A | 10/1932 | Tomlinson |
| 3,079,606 A | 3/1963 | Bobrov et al. |
| 3,193,165 A | 7/1965 | Akhalaya et al. |
| 3,256,875 A | 6/1966 | Tsepelev et al. |
| 3,388,847 A | 6/1968 | Kasulin et al. |
| 3,490,675 A | 1/1970 | Green et al. |
| 3,494,533 A | 2/1970 | Green et al. |
| 3,552,626 A | 1/1971 | Astafiev et al. |
| 3,618,842 A | 11/1971 | Bryan |
| 3,662,939 A | 5/1972 | Bryan |
| 3,815,476 A | 6/1974 | Green et al. |
| 3,858,577 A | 1/1975 | Bass et al. |
| 3,859,986 A | 1/1975 | Okada et al. |
| 4,071,029 A | 1/1978 | Richmond et al. |
| 4,085,756 A | 4/1978 | Weaver |

(List continued on next page.)

FOREIGN PATENT DOCUMENTS

| | | |
|---|---|---|
| DE | 33 00 768 | 7/1984 |
| EP | 0 116 220 | 8/1984 |
| EP | 0 121 474 | 10/1984 |
| EP | 0 156 774 | 10/1985 |
| EP | 0 216 532 | 4/1987 |

(List continued on next page.)

Primary Examiner—Edward K. Look
Assistant Examiner—John K Fristoe, Jr.
(74) Attorney, Agent, or Firm—Kenyon & Kenyon (57) ABSTRACT

A fibrin injection mechanism for use in combination with an anastomosing and stapling attachment for an electromechanical device driver comprises a cylindrical dispensing chamber adjacent the cylindrical blade of the attachment and containing a sac filled with fibrin, a plurality of channels extending within the blade communicating between the dispensing chamber and the cutting edge of the blade, such that when the turning drive shaft is activated, the staple driver of the attachment moves forward to push a plurality of staples through corresponding staple ports and against the anvil of the attachment to pass through and staple together the target tissue, while the blade driver of the attachment moves forward to cut the unwanted residual tissue (post stapling), while a plunger (delivery) driver moves forward through the dispensing chamber to compress the sac to its break point, releasing the fluid medication into the dispensing chamber, and eventually pushing the medication though the channels to deliver the fibrin to the cutting edge of the blade and thus to the site of the newly stapled target tissue to accelerate the healing process.

25 Claims, 4 Drawing Sheets

U.S. PATENT DOCUMENTS

| | | |
|---|---|---|
| 4,198,960 A | 4/1980 | Utsugi |
| 4,198,982 A | 4/1980 | Fortner et al. |
| 4,202,479 A | 5/1980 | Razgulov et al. |
| 4,207,898 A | 6/1980 | Becht |
| 4,250,873 A | 2/1981 | Bonnet |
| 4,273,109 A | 6/1981 | Enderby |
| 4,273,111 A | 6/1981 | Tsukaya |
| 4,286,585 A | 9/1981 | Ogawa |
| 4,289,133 A | 9/1981 | Rothfuss |
| 4,304,236 A | 12/1981 | Conta et al. |
| 4,310,115 A | 1/1982 | Inoue |
| 4,319,576 A | 3/1982 | Rothfuss |
| 4,351,466 A | 9/1982 | Noiles |
| 4,367,729 A | 1/1983 | Ogiu |
| 4,379,457 A | 4/1983 | Gravener et al. |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,473,077 A | 9/1984 | Noiles et al. |
| 4,476,863 A | 10/1984 | Kanshin et al. |
| 4,484,503 A | 11/1984 | Sitte et al. |
| 4,485,817 A | 12/1984 | Swiggett |
| 4,488,523 A | 12/1984 | Shichman |
| 4,499,895 A | 2/1985 | Takayama |
| 4,505,272 A | 3/1985 | Utyamyshev et al. |
| 4,505,414 A | 3/1985 | Filipi |
| 4,520,817 A | 6/1985 | Green |
| 4,535,773 A | 8/1985 | Yoon |
| 4,559,928 A | 12/1985 | Takayama |
| 4,573,468 A | 3/1986 | Conta et al. |
| 4,574,806 A | 3/1986 | McCarthy |
| 4,576,167 A | 3/1986 | Noiles |
| 4,589,412 A | 5/1986 | Kensey |
| 4,589,582 A | 5/1986 | Bilotti |
| 4,592,354 A | 6/1986 | Rothfuss |
| 4,593,679 A | 6/1986 | Collins |
| 4,603,693 A | 8/1986 | Conta et al. |
| 4,605,001 A | 8/1986 | Rothfuss et al. |
| 4,606,343 A | 8/1986 | Conta et al. |
| 4,610,383 A | 9/1986 | Rothfuss et al. |
| D286,567 S | 11/1986 | Lichtman et al. |
| 4,631,052 A | 12/1986 | Kensey |
| 4,646,745 A | 3/1987 | Noiles |
| 4,655,673 A | 4/1987 | Hawkes |
| 4,667,673 A | 5/1987 | Li |
| 4,671,445 A | 6/1987 | Barker et al. |
| 4,672,961 A | 6/1987 | Davies |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,742,815 A | 5/1988 | Ninan et al. |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,771,774 A | 9/1988 | Simpson et al. |
| 4,776,506 A | 10/1988 | Green |
| 4,781,186 A | 11/1988 | Simpson et al. |
| 4,784,137 A | 11/1988 | Kulik et al. |
| 4,813,928 A | 3/1989 | Abe et al. |
| 4,817,847 A | 4/1989 | Redtenbacher et al. |
| 4,819,632 A | 4/1989 | Davies |
| 4,867,158 A | 9/1989 | Sugg |
| 4,873,977 A | 10/1989 | Avant et al. |
| 4,887,599 A | 12/1989 | Muller |
| 4,890,602 A | 1/1990 | Hake |
| 4,892,244 A | 1/1990 | Fox et al. |
| 4,893,613 A | 1/1990 | Hake |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,928,699 A | 5/1990 | Sasai |
| 4,930,494 A | 6/1990 | Takehana et al. |
| 4,936,845 A | 6/1990 | Stevens |
| 4,955,882 A | 9/1990 | Hakky |
| 4,957,499 A | 9/1990 | Lipatov et al. |
| 4,962,877 A | 10/1990 | Hervas |
| 4,976,688 A | 12/1990 | Rosenblum |
| 4,976,710 A | 12/1990 | Mackin |
| 4,982,726 A | 1/1991 | Taira |
| 4,994,060 A | 2/1991 | Rink et al. |
| 4,995,877 A | 2/1991 | Ams et al. |
| 5,005,749 A | 4/1991 | Aranyi |
| 5,040,715 A | 8/1991 | Green et al. |
| 5,059,203 A | 10/1991 | Husted |
| 5,071,430 A | 12/1991 | de Salis et al. |
| 5,077,506 A | 12/1991 | Krause |
| 5,104,025 A | 4/1992 | Main et al. |
| 5,133,359 A | 7/1992 | Kedem |
| 5,133,729 A | 7/1992 | Sjostrom |
| 5,139,513 A | 8/1992 | Segato |
| 5,170,925 A | 12/1992 | Madden et al. |
| 5,171,247 A | 12/1992 | Hughett et al. |
| 5,171,251 A | 12/1992 | Bregen et al. |
| 5,192,292 A | 3/1993 | Cezana et al. |
| 5,197,649 A | 3/1993 | Bessler et al. |
| 5,201,325 A | 4/1993 | McEwen et al. |
| 5,205,459 A | 4/1993 | Brinkerhoff et al. |
| 5,207,691 A | 5/1993 | Nardella |
| 5,221,279 A | 6/1993 | Cook et al. |
| 5,224,951 A | 7/1993 | Freitas |
| 5,226,426 A | 7/1993 | Yoon |
| 5,237,884 A | 8/1993 | Seto |
| 5,249,583 A | 10/1993 | Mallaby |
| 5,258,007 A | 11/1993 | Spetzler et al. |
| 5,258,008 A | 11/1993 | Wilk |
| 5,261,877 A | 11/1993 | Fine et al. |
| 5,267,997 A | 12/1993 | Farin et al. |
| 5,271,543 A | 12/1993 | Grant et al. |
| 5,271,544 A | 12/1993 | Fox et al. |
| 5,275,322 A | 1/1994 | Brinkerhoff et al. |
| 5,279,565 A | 1/1994 | Klein et al. |
| 5,285,945 A | 2/1994 | Brinkerhoff et al. |
| 5,289,963 A | 3/1994 | McGarry et al. |
| 5,290,299 A | 3/1994 | Fain et al. |
| 5,292,053 A | 3/1994 | Bilotti et al. |
| 5,312,023 A | 5/1994 | Green et al. |
| 5,318,221 A | 6/1994 | Green et al. |
| 5,326,013 A | 7/1994 | Green et al. |
| 5,330,486 A | 7/1994 | Wilk |
| 5,333,773 A | 8/1994 | Main et al. |
| 5,342,299 A | 8/1994 | Snoke et al. |
| 5,342,382 A | 8/1994 | Brinkerhoff et al. |
| 5,344,420 A | 9/1994 | Hilal et al. |
| 5,350,104 A | 9/1994 | Main et al. |
| 5,354,266 A | 10/1994 | Snoke |
| 5,368,607 A | 11/1994 | Freitas |
| 5,380,321 A | 1/1995 | Yoon |
| 5,383,880 A | 1/1995 | Hooven |
| 5,395,030 A | 3/1995 | Kuramoto et al. |
| 5,395,033 A | 3/1995 | Byrne et al. |
| D357,535 S | 4/1995 | Grant et al. |
| 5,403,312 A | 4/1995 | Yates et al. |
| 5,403,327 A | 4/1995 | Thornton et al. |
| 5,411,508 A | 5/1995 | Bessler et al. |
| 5,413,267 A | 5/1995 | Solyntjes et al. |

| | | | | | | |
|---|---|---|---|---|---|---|
| 5,425,738 A | 6/1995 | Gustafson et al. | | 5,997,510 A | 12/1999 | Schwemberger |
| 5,433,721 A | 7/1995 | Hooven et al. | | 6,007,531 A | 12/1999 | Snoke et al. |
| 5,437,636 A | 8/1995 | Snoke et al. | | 6,010,493 A | 1/2000 | Snoke |
| 5,441,507 A | 8/1995 | Wilk | | 6,010,512 A | 1/2000 | Chu et al. |
| 5,467,911 A | 11/1995 | Tsuruta et al. | | 6,017,322 A | 1/2000 | Snoke et al. |
| 5,482,197 A | 1/1996 | Green et al. | | 6,086,600 A | 7/2000 | Kortenbach |
| 5,485,947 A | 1/1996 | Olson et al. | | 6,099,466 A | 8/2000 | Sano et al. |
| 5,496,269 A | 3/1996 | Snoke | | 6,119,913 A | 9/2000 | Adams et al. |
| 5,518,163 A | 5/1996 | Hooven | | 6,126,058 A | 10/2000 | Adams et al. |
| 5,518,164 A | 5/1996 | Hooven | | 6,126,591 A | 10/2000 | McGarry et al. |
| 5,531,687 A | 7/1996 | Snoke et al. | | 6,193,129 B1 | 2/2001 | Bittner et al. |
| 5,533,661 A | 7/1996 | Main et al. | | 6,209,773 B1 | 4/2001 | Bolduc et al. |
| 5,549,565 A | 8/1996 | Ryan et al. | | 6,248,093 B1 * | 6/2001 | Moberg .................... 604/131 |
| 5,599,347 A | 2/1997 | Hart et al. | | | | |
| 5,639,008 A | 6/1997 | Gallagher et al. | | FOREIGN PATENT DOCUMENTS | | |
| 5,653,374 A | 8/1997 | Young et al. | | EP | 0 399 701 | 11/1990 |
| 5,662,673 A | 9/1997 | Kieturakis | | EP | 0 514 139 | 11/1992 |
| 5,667,517 A | 9/1997 | Hooven | | EP | 0 536 903 | 4/1993 |
| 5,693,031 A | 12/1997 | Ryan et al. | | EP | 0 539 762 | 5/1993 |
| 5,697,940 A | 12/1997 | Chu et al. | | EP | 0 552 050 | 7/1993 |
| 5,735,861 A | 4/1998 | Peifer et al. | | EP | 0 593 920 | 4/1994 |
| 5,749,893 A | 5/1998 | Vidal et al. | | EP | 0 621 006 | 10/1994 |
| 5,758,814 A | 6/1998 | Gallagher et al. | | FR | 2660851 | 10/1991 |
| 5,779,130 A | 7/1998 | Alesi et al. | | GB | 2 044 108 | 10/1980 |
| 5,782,396 A | 7/1998 | Mastri et al. | | GB | 2180455 | 4/1987 |
| 5,797,835 A | 8/1998 | Green | | NL | 77 11 347 | 4/1979 |
| 5,797,944 A | 8/1998 | Nobles et al. | | WO | WO 82/03545 | 10/1982 |
| 5,846,221 A | 12/1998 | Snoke et al. | | WO | WO 83/00992 | 3/1983 |
| 5,857,996 A | 1/1999 | Snoke | | WO | WO 90/05489 | 5/1990 |
| 5,860,953 A | 1/1999 | Snoke et al. | | WO | WO 90/05491 | 5/1990 |
| 5,868,760 A | 2/1999 | McGuckin, Jr. | | WO | WO 91/07136 | 5/1991 |
| 5,871,471 A | 2/1999 | Ryan et al. | | WO | WO 92/16141 | 10/1992 |
| 5,925,055 A | 7/1999 | Adrian et al. | | WO | WO 93/08754 | 5/1993 |
| 5,954,259 A | 9/1999 | Viola et al. | | WO | WO 95/35065 | 12/1995 |
| 5,984,919 A | 11/1999 | Hilal et al. | | WO | WO 97/12555 | 4/1997 |
| 5,989,215 A | 11/1999 | Delmotte et al. | | WO | WO 99/20328 | 4/1999 |
| 5,989,274 A | 11/1999 | Davison et al. | | | | |
| 5,993,378 A | 11/1999 | Lemelson | | * cited by examiner | | |

FLUID DELIVERY DEVICE FOR USE WITH ANASTOMOSING STAPLING, AND RESECTING INSTRUMENTS

CROSS-REFERENCE TO RELATED APPLICATIONS

This application is a continuation of U.S. Patent Application Serial No. 09/510,933, which was filed on Feb. 22, 2000, now U.S. Pat. No. 6,488,197 each of which is expressly incorporated herein in its entirety by reference thereto.

BACKGROUND OF THE INVENTION

1. Field of the Invention

The present invention relates generally to a fluid delivery device for use with anastomosing, stapling, and resecting surgical tools, and more specifically to a fibrin injection mechanism by which such tools may deliver fibrin to the stapling and cutting site of a resected colon.

2. Description of the Prior Art

Upon identification of cancerous or other anomalous tissue in the gastrointestinal tract, surgical intervention is often prescribed. The field of cancer surgery, and more specifically, the surgical procedure by which a section of the gastrointestinal tract which includes cancerous or anomalous tissue is resected, includes a number of uniquely designed instruments. In combination with a description of the present instrumentation and their functions, a description of the state of the art in this surgical procedure shall also be provided.

The first question which must be answered when determining how to treat gastrointestinal cancer relates to the specific location of the cancerous tissue. This is very important insofar as the instruments which are provided in the present art have limitations relating to how far they may be inserted into the gastrointestinal tract. If the cancerous tissue is too far up the colon, for example, then the standard instrumentation provided is unusable, thus requiring special accommodations. These accommodations generally increase the risk of contamination of the surrounding tissues with bowel contents, increase the length of the surgery and the corresponding need for anesthesia, and eliminate the benefits of precise anastomosing and stapling which comes from utilizing a mechanized device.

More specifically, in the event that the cancerous tissue is located at a position in the colon which is accessible by the present instrumentation, the patient's abdomen is initially opened to expose the bowel. The surgeon then utilizes a linear cutter and stapling device which cuts the tube of the colon on either side of the cancerous tissue, thereby creating two stapled ends of the bowel (a distal end which is directed toward the anus, and the proximal end which is closest to the small intestine). This is done in order to temporarily minimize contamination.

Figure 1:
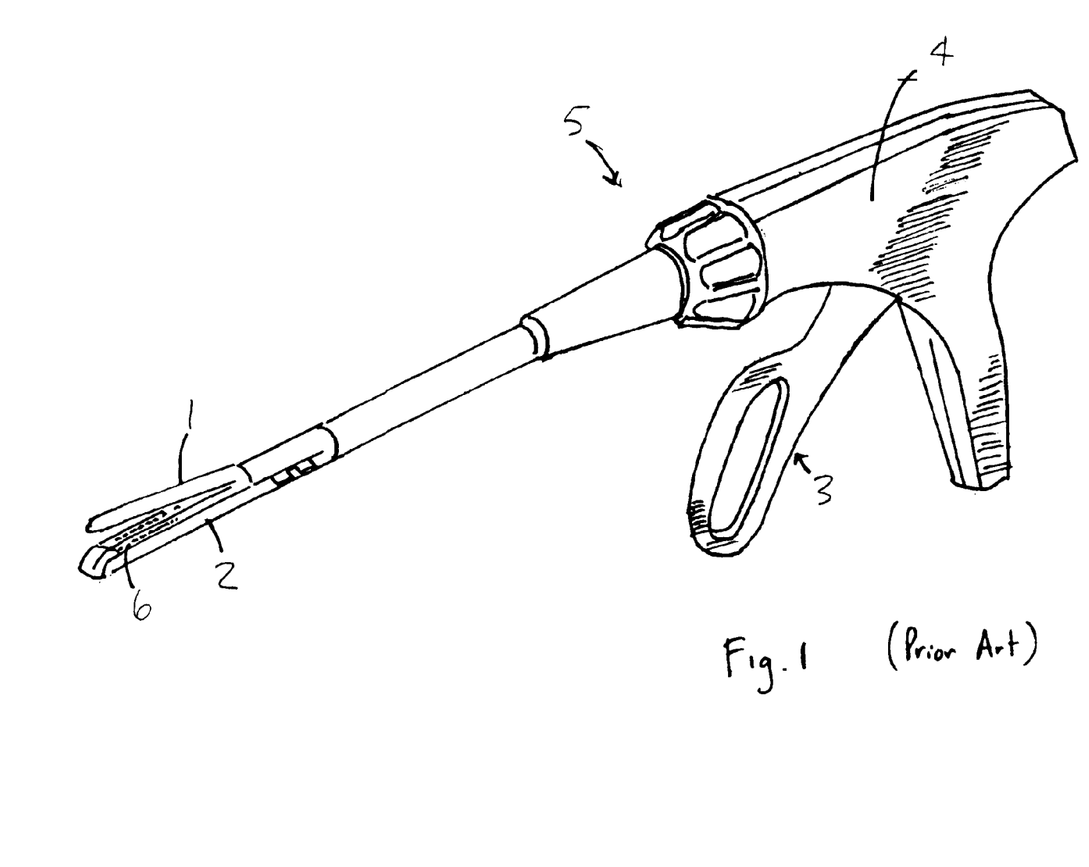
FIG. 1 is a side perspective view of a linear clamping and stapling instrument of the prior art.

More particularly, referring to FIG. 1, the bowel is placed between the scissoring elements 1, 2 at the tip of the linear stapling instrument 5. By squeezing the trigger 3 in the handle 4 of the device, the surgeon causes the scissoring elements 1, 2 to come together. A second trigger (or a secondary action of the same trigger) is then actuated to drive a series of staples 6 through the clamped end of the colon, thereby closing and transecting the ends.

The surgeon then partially opens the proximal end and inserts the removable anvil portion of an anastomosing and stapling instrument into the exposed proximal end. This step, as well as those of the remainder of the surgical procedure, are related to the functioning of this surgical instrument. More particularly, and with respect to FIG. 2, the surgeon begins by taking the instrument 7 and manually turning the dial 8 at the base of the handle 9 which causes the anvil head 10 at the opposite end to advance forward. The surgeon continues to turn the dial 8 until the anvil head 10 advances to its most extreme extended position. This manual turning requires nearly thirty full rotations. Once fully extended, the anvil head of the instrument is decoupled therefrom and is inserted into the partial opening of the proximal end such that the coupling post extends outwardly therethrough. This partial opening of the proximal end is then sutured closed. The extending shaft 11 of the anastomosing and stapling instrument 7 is then inserted and advanced into the lower colon, transanally, until the coupling stem 12 thereof extends through the stapled distal end. The surgeon then joins the coupling ends of the anvil and shaft together and begins to manually rotate the dial in the handle again, this time bringing the anvil head closer to the end 13 of the shaft.

Figure 2:
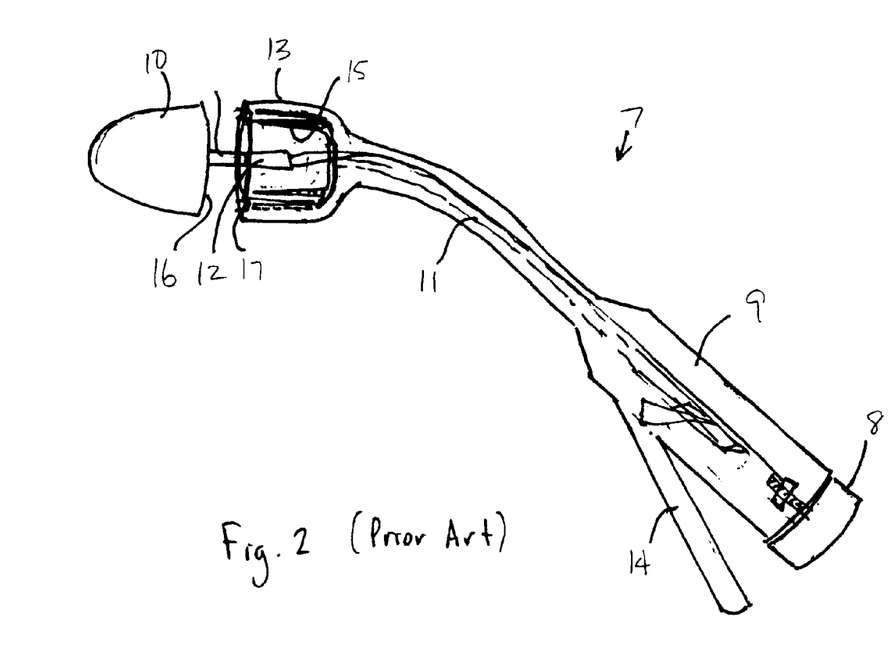
FIG. 2 is a side perspective view of an anastomosing and stapling instrument of the prior art.

Once the anvil head and shaft are brought close together, after the surgeon has manually rotated the dial another thirty times, a grip-style trigger 14 in the handle is manually actuated. This actuation causes a circular blade 15 to advance axially out from the tip of the shaft, and into contact with the opposing face 16 of the anvil 10. The blade cuts through the stapled-closed ends of the proximal and distal ends of the colon, thereby also cutting a new pair of ends of the proximal and distal portions of the colon. The tissue which has been severed is held in an interior volume at the end of the shaft.

In lock step with the cutting, the freshly opened ends are joined together by a series of staples 17 which are advanced through holes in the perimeter of the tip of the shaft (being pressed against and closed by the opposing face of the anvil). The coupled shaft and anvil are then withdrawn from the patient.

As with many such devices of the prior art, all of the above devices are considered fully disposable, and are, in fact, thrown away after a single use. They are complicated devices, having multiple moving parts, requiring substantial structural integrity and, therefore, expense in manufacturing. The fact that they are used only once, and no part can be used again render the use of such devices expensive and wasteful of resources.

In addition to this failure, as can be readily observed from the preceding descriptions, the prior art devices suffer from numerous other limitations which would be desirable to overcome. These include the requirement that the surgeon manually actuate a number of different functions (including those associated with the dial and trigger of the anastomosing and stapling instrument and the multiple triggers of the cutting and stapling instrument).

Another failure is that the prior art devices provide no means to allow the delivery of fluid to the site of the freshly cut tissue. Medicine or other substances which accelerate the healing process, if delivered to the site simultaneous with or subsequent to the stapling and cutting process, could speed healing of the tissue or perform other medical functions. One such substance is fibrin, which is the principal protein component of connective tissue, and serves as the fundamental element of the tissue-mending process, specifically the process of scar formation at the joining of two previously separate tissues. Therefore, the ability to inject such a substances at the site of the freshly stapled and cut tissue would provide an advantage over the prior art devices, which make no provision for such delivery.

Therefore, it is a principal object of the present invention to provide a fluid delivery device which can effect such medicine delivery at the stapling and cutting site of targeted tissue.

It is also a principal object of the present invention to provide such a fluid delivery device in a form integral with an instrument for cutting, anastomosing, and stapling, which reduces the waste of resources by permitting the reuse of portions thereof.

It is further an object of the present invention to provide such a fluid delivery device which reduces the requirements for the surgeon to manually actuate different components and mechanisms.

Other objects of the present invention shall be recognized in accordance with the description thereof provided hereinbelow, and in the Detailed Description of Preferred Embodiments in conjunction with the remaining Figures.

SUMMARY OF THE INVENTION

The preceding objects of the invention are provided by a fluid delivery mechanism which is integral with an anastomosing and stapling attachment of an electromechanical driver assembly which couples to the anastomosing and stapling attachment. More particularly, the present invention comprises a dispensing chamber containing a fluid, a channel communicating between a treatment site and the dispensing chamber, and a delivery or plunger driver traveling within the dispensing chamber with a force equal to or greater than the force needed to push the fluid through the channel. In the preferred embodiment, the present invention is used in combination with an anastomosing and stapling attachment of an electromechanical device driver. It comprises a cylindrical dispensing chamber adjacent the cylindrical blade of the attachment. The dispensing chamber contains a sac filled with fibrin. A plurality of channels extend within the blade and communicate between the dispensing chamber and the cutting edge of the blade. A turning drive shaft of the attachment which is connected to the electromechanical driver drives a staple driver, a blade driver, and a delivery (plunger) driver. When the turning drive shaft is activated (via the trigger on the electromechanical driver handle), the staple driver moves forward to push a plurality of staples through corresponding staple ports and against the anvil of the attachment to pass through and staple together the target tissue. Meanwhile, by the same activating mechanism, the blade driver of the attachment moves forward to cut the unwanted residual tissue (the tissue which is no longer needed). Also meanwhile, the plunger driver moves forward through the dispensing chamber to compress the sac to its break point. When the sac breaks, the fluid is released into the dispensing chamber. The plunger driver continues forward, pushing the fluid into and through the channels in the blade, delivering the medicine to the cutting edge of the blade and thus to the site of the newly stapled target tissue to begin acceleration the healing process.

Figure 3:
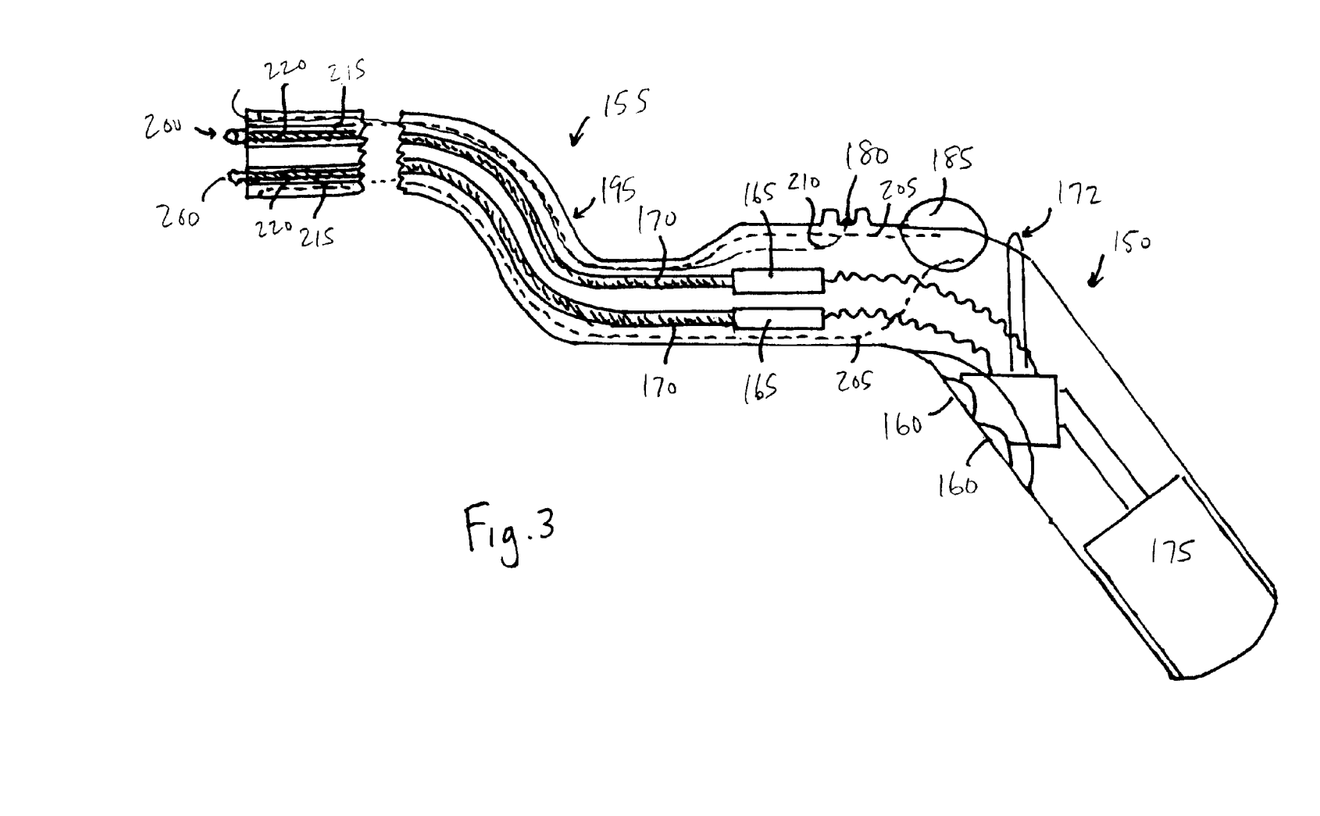
FIG. 3 is a side view of a handle and flexible shaft of an electromechanical device driver which is used to drive the anastomosing and stapling attachment described herein.

Specifically, with respect to the electromechanical driver, the driver is shown in FIG. 3 and has a handle 150 and a flexible drive shaft 155. The handle 150 has a pistol grip-styled design, having one or more, and preferably two, finger triggers 160 which are independently coupled to at least one, and preferably two separate motors 165 which each turn separate flexible drive shafts 170 (described more fully, hereinbelow). The motors 165 are each dual direction motors, and are coupled to a manual drive switch 172 to the top of the handle, by which the user can selectively alter the turning direction of each motor. This dual direction capacity may be most simply achieved by selecting motors which turn in a direction corresponding to the direction of current, and actuation of the drive switches alters the direction of the current accordingly. In this example, the power source 175 supplying the motors must be a direct current source, such as a battery pack (and most desirably, a rechargeable battery pack). In the event that the device should be useable with an alternating current, either a transformer can be included, or a more sophisticated intermediate gearing assembly may be provided. In conjunction with the present description, the embodiments of the present invention which will be described utilize a rechargeable battery pack providing a direct current.

In addition to the motor components, the handle further includes several other features, including a remote status indicator 180, a shaft steering means 185, and an on/off switch (not shown). First, the remote status indicator may comprise an LCD (or similar read out device) by which the user may gain knowledge of the position of components (for example whether a clamping element is in the proper position prior to the driving of the staples). Second, the handle also includes a manually actuateable steering means, for example, a joystick or track ball, for directing the movement of the flexible shaft (by means of steering wires implanted in the shaft portion described more fully hereinbelow). Finally, the handle may include an additional electrical power supply and an on/off switch for selectively supplying electrical power to the attachments.

More particularly, with respect to the flexible shaft, the shaft comprises a tubular sheath 195, preferably formed of a simple elastomeric material which is tissue compatible and which is sterilizable (i.e., is sufficiently rugged to withstand an autoclave). Various lengths of this shaft may be provided. The flexible shaft and the handle portions can be separable. If separable, the interface between the proximal end of the shaft and the distal end of the handle should include a coupling means for the drive components.

Specifically regarding the drive components of the shaft, within the elastomeric sheath are a pair of smaller fixed tubes 215 which each contain a flexible drive shaft 220 which is capable of rotating within the tube. The flexible drive shaft, itself, translates a torque from the motor in the handle to the distal end of the shaft, but is flexible enough to be bent, angled, curved, etc. as the surgeon deems necessary to "snake" through the colon of the patient. In order for the distal end of the drive shaft to couple with an attachment, such as the anastomosing and stapling attachment discussed herein, however, the distal tips of the drive shafts must have a conformation which permits the continued translation of torque. For example, the distal tips 200 of the drive shafts may be hexagonal, thereby fitting into a hexagonal recess in the coupling interface of the attachment. Appropriate gearing mechanisms may be provided at the distal end of the shaft, or in the interfacing portion of the attachment, to ensure that the appropriate torque is provided to the attachment.

As suggested above, in conjunction with the manually actuateable steering means mounted to the handle, the sheath further includes at least two steering wires 205 which are flexible, but are coupled to the inner surface of the sheath near the distal end thereof. The steering wires may be axially translated relative to one another by actuation of the steering means, which action causes the sheath to bend and curve accordingly.

Also as suggested above, in conjunction with the LCD indicator of the handle, the shaft further contains an electrical lead 210 for coupling to the attachments. This electrical lead channels a signal from the attachment to the handle for indicating the status of the attachment (for example, whether the anvil portion is in close proximity to the SBR portion, so that the surgeon knows it is safe to staple). Similarly, a second electrical lead may be provided to supply power to separate aspects of the attachment if so required.

Referring now to the fluid delivery device of the present invention, described here in conjunction with an anastomosing and stapling attachment, a preferred embodiment and an alternative embodiment are described hereinbelow as examples of the different variations which could be constructed for the equivalent purpose.

The anastomosing and stapling attachment comprises an anvil portion, and a staple, blade and reservoir portion (SBR portion), which includes a pair of turning drive shafts which are coupleable to the drive components of the shaft element described above, and a corresponding pair of advancing and retracting nuts mounted to the turning drive shafts, but which are prevented from rotating and therefore linearly advance and retract along the shafts when they turn.

The anvil portion is bullet shaped, having a blunt nosed top portion, a flat cutting support surface on the bottom, and a freely rotating coupling post extending axially from the bottom surface. This coupling post is designed to be selectively coupleable and removable from the corresponding nut mounted to one of the turning drive shafts.

The SBR portion is cylindrical in shape, forming a housing which has a hollow interior. It is this hollow interior which forms the reservoir. On the axially outward facing surface of the cylindrical wall of the housing are a series of staple ports, through which the staples of the device are discharged. A series of staple drivers are mounted within the cylindrical walls, beneath the staple ports, for driving the staples therethrough. More accurately, the staple drivers are a series of protuberances on the outer edge of a single cylindrical component which seats in the wall of the SBR portion. The staples, prior to being discharged, are mounted in the holes; and they are advanced through the holes by the forward motion of the staple driver and the protuberances thereof.

The blade is similarly cylindrical, and seats in the inside of the housing, against the inner surface of the wall thereof. Both the blade and the staple driver are mounted to the second nut, which is, in turn, mounted to the other turning drive shaft. As the tuning drive shaft rotates, the nut (which is constrained against rotating) advances along the shaft, thus linearly advancing the blade and staple driver. The blade and the staple driver are, therefore, selectively advanceable axially outward from the housing, in accordance with actuation of the appropriate trigger on the handle.

In order to accelerate the healing process, the attachment is fitted with the present invention, i.e., a mechanism for delivering fluid, medicine or a healing substance such as fibrin at the cutting and stapling site, immediately after the cutting and stapling action described above. This mechanism can take on any of several embodiments, two of which are described hereinbelow as examples. Generally, the fibrin is contained within a sac formed by a thin skin or membrane. The sac is contained within a dispensing chamber through which travels a delivery or plunger driver. Once the blade and the staple driver reach the anvil, the blade and staple driver are stopped by the anvil, simultaneously performing the stapling and cutting actions described above. The delivery or plunger driver, coupled to the second nut along with the blade and the staple driver, continues on, driven axially outward from the housing, compressing the sac, causing pressure to build in the sac. Once the pressure reaches the break point of the membrane, the fibrin is released and is transferred from the sac to the cutting and stapling site via channels in the blade.

In practice, this attachment is utilized once the section of the colon which is to be removed has been resected (but prior to the linear clamping and stapling step is complete), in the following manner. The surgeon begins by coupling the anastomosing and stapling attachment to the electromechanical driver and advancing the anvil portion to its fullest extent. The anvil head is then removed and inserted into the exposed proximal end. This proximal end is then stapled closed (with the coupling post protruding from the stapled proximal end). The surgeon then advances the shaft and the SBR portion of the attachment up the colon until it extends through the stapled distal end of the colon. The surgeon then couples the anvil to the advancing and retracting nut of the corresponding drive shaft. Subsequent triggering of the motor in the handle causes the anvil to retract toward the SBR portion. When the anvil portion and the SBR portion have come close enough to drive the blade and staple driver, subsequent actuation of the other trigger on the handle causes the corresponding other turning drive shaft to advance the blade and staple driver toward the flat cutting support surface of the anvil portion. The blade cuts through the stapled-closed ends of the colon, leaving the tissue which has been severed in the interior reservoir. Simultaneous with the cutting, the freshly opened ends are joined together by the series of staples which are advanced through holes in the perimeter edge of the SBR (being pressed against and closed by the opposing face of the anvil). Shortly thereafter, as described above, the plunger driver advances, increasing pressure in the membrane which contains the fibrin. Once the membrane breaks, the fibrin is released and transferred to the cutting and stapling site through holes in the blade. The attachment and the flexible shaft are then withdrawn from the patient.

It should be noted that the present invention may be used in conjunction with a stapling attachment only, such that the dispensing chamber is adjacent the stapler, and the channels extend within or adjacent the stapler to deliver the medicine or healing substance such as fibrin to the stapling site. This may be used if the cutting action is not needed. Inasmuch as the present invention can be used for applications and in conjunction with devices not related to the anastomosing and stapling attachment, or even colon resecting tools, but rather can be used for applications involving and in conjunction with other surgical devices, the present invention can be used alone, or with a blade, or with a stapler, or with other devices or combinations of devices.

A DETAILED DESCRIPTION OF THE PREFERRED EMBODIMENT

While the present invention will be described more fully hereinafter with reference to the accompanying drawings, in which particular embodiments are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 4:
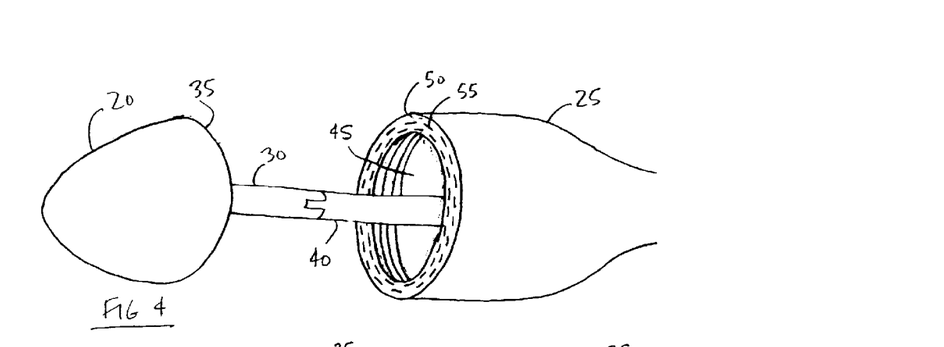
FIG. 4 is a perspective view of an anastomosing and stapling attachment having an integrated medicine delivery device of the present invention.
Figure 5:
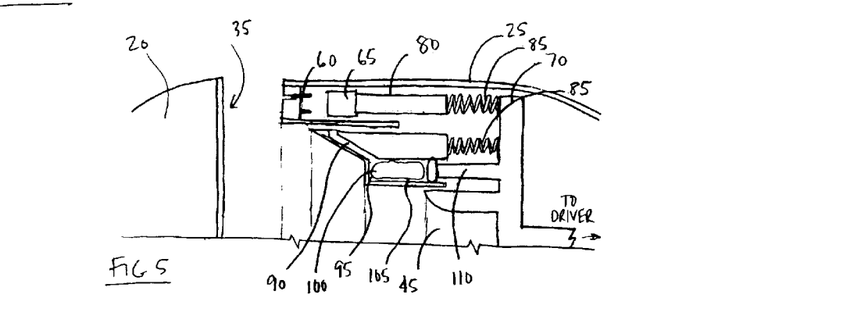
FIG. 5 is a side cutaway view of a first embodiment of the medicine delivery device of the present invention integral with an anastomosing and stapling attachment.
Figure 6:
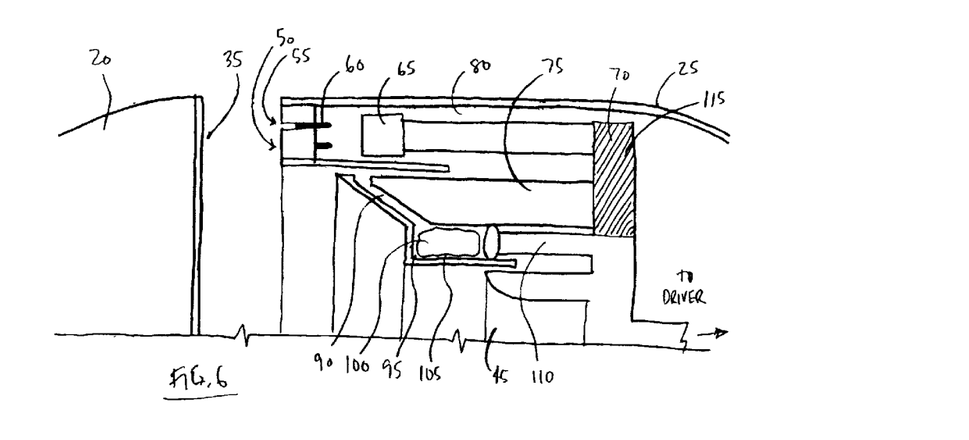
FIG. 6 is a side cutaway view of a second embodiment of the medicine delivery device of the present invention integral with an anastomosing and stapling attachment.

A preferred embodiment of the fluid delivery device for an anastomosing and stapling attachment according to the present invention is illustrated in FIGS. 4–6. More particularly, referring now to FIG. 4, a perspective exterior view of an anastomosing and stapling attachment in an extended position is shown. The anvil portion 20 and the staple, blade, and reservoir (SBR) portion 25 are connected by a coupling post 30 which extends from the flat cutting support surface 35 of the anvil portion 20 and is selectively coupleable and removable from the corresponding nut mounted to one of the turning drive shafts 40 of the SBR portion 25.

Referring now also to FIG. 5, a cutaway view of the interior of the SBR portion 25 is shown. The SBR portion 25 is cylindrical in shape, and has a hollow interior, or reservoir 45. A stapling surface 50 faces axially outward toward the cutting support surface 35 of the anvil portion 20, and contains a series of staple ports 55, through which staples 60 are discharged. A series of staple drivers 65 are mounted within a staple driver shaft 80, behind corresponding staple ports 55, for driving the staples 60 therethrough. More accurately, the staple drivers 65 are a series of protuberances on the outer edge of a driving cylinder 70 which seats in the SBR portion 25 and which is connected to the second drive shaft (not shown) of the SBR portion 25. The staples 60, prior to being discharged, are mounted behind the staple ports 55 as shown and are advanced through the ports 55 by the forward motion of the staple drivers 65 and the protuberances thereof.

The blade 75 is similarly cylindrical, and seats in the SBR portion adjacent the staple driver shaft 80. Both the blade 75 and the staple drivers 65 are mounted via semi-rigid springs 85 to the driving cylinder 70 as shown, which is connected to the second drive shaft (not shown) of the SBR portion 25. The nature of the semi-rigidity of the springs 85 will be explained below. The blade 75 further has a series of channels 90 communicating with a dispensing chamber 95. The chamber 95 extends from the inner side of the blade 75 and spans the circumference of the blade 75, while the channels 90 are tubular in nature and are positioned at intervals along the length of the blade 75, so as to maintain the structural integrity of the blade 75 while it is being used for cutting. Within the chamber 95 is contained a sac 100 formed by a sealed membrane 105 and which contains fibrin (not noted). Immediately behind the sac 100 is positioned a plunger driver 110 which is mounted to the driving cylinder 70 as shown.

Referring now to FIG. 6, the preferred embodiment of the fluid delivery device of an anastomosing and stapling attachment according to the present invention is illustrated. All components are as described above for FIG. 5, however, the staple drivers 65 and blade 75 are mounted to the driving cylinder 70 not by springs 85, but rather by a break-away extension 115 as shown in shade.

In operation (operation of both embodiments will be described below), the attachment is utilized once the section of the colon which is to be removed has been resected (but prior to the linear clamping and stapling step is complete). The surgeon begins by coupling the anastomosing and stapling attachment to the electromechanical driver and advancing the anvil portion 20 to its fullest extent via a triggering of the motor (not shown) in the handle (not shown). The anvil portion 20 is then decoupled from the electromechanical driver and inserted into the exposed proximal end. This proximal end is then stapled closed (with the coupling post 30 protruding from the stapled proximal end). The surgeon then advances the first turning drive shaft 40 and the SBR portion 25 of the attachment up the colon until it extends through the stapled distal end of the colon. The surgeon then re-couples the anvil portion 20, via the coupling post 30, to the first turning drive shaft 40. Subsequent reverse triggering of the motor (not shown) in the handle (not shown) causes the anvil portion 20 to retract toward the SBR portion 25, thus bringing the stapled-closed proximal and distal ends of the colon together. When the anvil portion 20 and the SBR portion 25 have come close enough to drive the blade 75 and staple driver 65, subsequent actuation of a second trigger (not shown) on the handle (not shown) causes the corresponding second turning drive shaft (not shown) to advance the blade 75 and staple driver 65 toward the flat cutting support surface 35 of the anvil portion 25. Once the blade 75 reaches the flat cutting support surface 35 of the anvil portion 25, the blade 75 cuts through the stapled-closed proximal and distal ends of the colon, leaving the now-severed tissue in the reservoir 45. Meanwhile, the staple drivers 65 (which have been advancing with the blade 75, yet positioned slightly behind the plane of the blade 75 as shown, in order to correctly time the stapling action to come immediately after the cutting action) reach the butts of the staples 60, and continue forward to push the staples 60 through the staple ports 55 and toward the stapling surface 50 and finally against the flat cutting support surface 35, which action bends the staple prongs to close the staples 60, thereby joining together the freshly cut-open proximal and distal ends of the colon. Meanwhile, the plunger driver 110 (which has been advancing with the blade 75 and staple drivers, yet positioned slightly behind the plane of the staple drivers 65 as shown, in order to correctly time the plunging action to come immediately after the stapling action) advances, reaching the sealed membrane 105 as the stapling action is completed.

In the first embodiment described above, thereafter the semi-rigid springs 85 (shown in FIG. 5) of the blade 75 and staple drivers 65 begin to compress from the forward motion of the second turning drive shaft (not shown). This allows the plunger driver 110 to continue its forward motion as well, and to thereby begin compression of the sealed membrane 105, thereby increasing pressure in the sealed membrane 105 which contains the fibrin (not noted). It should be noted that this embodiment allows re-use of the attachment, as the springs 85 will decompress after the pressure on the staple drivers 65 is released by retracting the second turning drive shaft. Once a new sac 100 is placed in the dispensing chamber 95, the attachment is ready for the next operation (assuming proper sterilization procedures have been followed).

Alternatively, in the second (preferred) embodiment described above, after the stapling action is completed, the break away extension 115 (shown in FIG. 6), from which extend the blade 75 and staple drivers 65, snaps off and its remnants are trapped within the body of the attachment as the forward motion of the second turning drive shaft (not shown) continues to move the plunger driver 110 forward. The forward motion of the plunger driver 110 begins compression of the sealed membrane 105, thereby increasing pressure in the sealed membrane 105 which contains the fibrin (not noted). It should be noted that the destruction of the break away extension 115 does not allow this attachment to be re-used.

Once the plunger driver 110 has compressed the membrane 105 to its maximum stress limit, the membrane 105 breaks, the fibrin is released, and passes through the channels 90 in the blade 75, and is thereby transferred to the cutting and stapling site (the freshly cut tissue). The blade 75, staple drivers 65, and plunger driver 110 can be withdrawn by reverse triggering the second turning drive shaft (not shown). The attachment and the flexible shaft are then withdrawn from the patient.

While there has been described and illustrated specific embodiments of new and novel fluid delivery devices, it will be apparent to those skilled in the art that variations and modifications are possible without deviating from the broad spirit and principle of the present invention which shall be limited solely by the scope of the claims appended hereto.

What is claimed is:

1. A fluid delivery device, comprising:
   a dispensing chamber configured to contain a fluid;
   a channel arranged to communicate between a treatment site and the dispensing chamber;
   a sac arranged within the dispensing chamber and configured to enclose the fluid; and
   a delivery driver configured to travel within the dispensing chamber with a force equal to or greater than a force needed to push said fluid through said channel and equal to or greater than a force needed to compress and break the sac within the dispensing chamber.

2. A fluid delivery device, comprising:
   a dispensing chamber configured to contain a fluid;
   a channel arranged to communicate between a treatment site and the dispensing chamber and arranged to communication with a cutting edge of a blade; and
   a delivery driver configured to travel within the dispensing chamber with a force equal to or greater than a force needed to push the fluid through the channel.

3. The device according to claim 2, wherein the dispensing chamber is arranged adjacent the blade.

4. The device according to claim 3, further comprising a blade driver arranged to drive the blade, the blade driver including a compressible portion, wherein the delivery driver is rigid.

5. The device according to claim 4, wherein the compressible portion includes a spring.

6. The device according to claim 3, further comprising a blade driver configured to drive the blade, the blade driver including a break-away portion, wherein the delivery driver is rigid and a rigidity of the break-away portion is less than a rigidity of the delivery driver.

7. The device according to claim 2, wherein the channel extends within the blade.

8. A fluid delivery device comprising:
   a dispensing chamber configured to contain a fluid, wherein the dispensing chamber is arranged adjacent to a stapler;
   a channel arranged to communicate between a treatment site and the dispensing chamber and arranged to communication with a cutting edge of a blade; and
   a delivery driver configured to travel within the dispensing chamber with a force equal to or greater than a force needed to push the fluid through the channel.

9. The device according to claim 8, further comprising a staple driver configured to drive the stapler, the staple driver including a compressible portion, wherein the delivery driver is rigid.

10. The device according to claim 9, wherein the compressible portion includes a spring.

11. The device according to claim 9, further comprising a staple driver configured to drive the stapler, the staple driver including a break-away portion, wherein the delivery driver is rigid and a rigidity of the break-away portion is less than a rigidity of the staple driver.

12. A fluid delivery device comprising:
    a dispensing chamber configured to contain a fluid;
    a channel arranged to communicate between a treatment site and the dispensing chamber and arranged to communication with a cutting edge of a blade, wherein the channel extends within a stapler; and
    a delivery driver configured to travel within the dispensing chamber with a force equal to or greater than a force needed to push the fluid through the channel.

13. A fluid delivery device comprising:
    a dispensing chamber configured to contain a fluid and arranged adjacent to a blade;
    a channel arranged to communicate between a treatment site and the dispensing chamber and arranged to communication with a cutting edge of the blade;
    a delivery driver configured to travel within the dispensing chamber with a force equal to or greater than a force needed to push the fluid through the channel; and
    a stapler arranged adjacent the blade and including a stapling surface, the blade including a cutting edge arranged to travel adjacent the stapling surface, the channel arranged to communicate with the cutting edge.

14. The device according to claim 13, further comprising a blade driver connected to the delivery driver and configured to drive the blade and a staple driver connected to the delivery driver and configured to drive the stapler, wherein the delivery driver is rigid.

15. The device according to claim 14, wherein at least one of the blade driver and the staple driver includes a compressible portion.

16. The device according to claim 14, wherein at least one of the blade driver and the staple driver includes a break-away portion having a rigidity less than a rigidity of the delivery driver.

17. The device according to claim 14, wherein the blade, the blade driver, the stapler, the staple driver, the dispensing chamber and the delivery driver are cylindrical and are arranged on a common cylindrical axis.

18. The device according to claim 17, further comprising a sac arranged within the dispensing chamber and arranged to enclose a fluid medication, the delivery driver configured to travel with a force equal to or grater than a force needed to compress and break the sac within the dispensing chamber.

19. A fluid delivery device, comprising:
    a dispensing chamber configured to contain a fluid;
    a channel arranged to communicate between a treatment site and the dispensing chamber and configured to communicate with a stapling surface of a stapler; and a delivery driver configured to travel within the dispensing chamber with a force equal or greater than a force needed to push the fluid through the channel.

20. A fluid delivery device, comprising:

a dispensing chamber configured to contain a fluid;

a channel arranged to communicate between a treatment site and the dispensing chamber;

a delivery driver configured to travel within the dispensing chamber with a force equal to or greater than a force needed to push the fluid through the channel; and a first rotatable drive shaft configured to selectively effect travel of the delivery driver in accordance with rotation thereof.

21. A fluid delivery device comprising:

a dispensing chamber configured to contain a fluid;

a channel arranged to communicate between a treatment site and the dispensing chamber;

a delivery driver configured to travel within the dispensing chamber with a force equal to or greater than a force needed to push the fluid through the channel;

a first rotatable drive shaft configured to selectively effect travel of the delivery driver in accordance with rotation thereof;

a stapler having an anvil portion and a staple driver; and a second rotatable drive shaft configured to selectively effect travel of the anvil portion relative to the staple driver;

wherein the first rotatable drive shaft is configured to selectively effect travel of the staple driver relative to the anvil portion.

22. The device according to claim 21, further comprising a blade, the first rotatable drive shaft configured to selectively effect travel of the blade relative to the anvil portion.

23. A method, comprising the steps of:

providing a fluid in a dispensing chamber;

rotating a first rotatable drive shaft to effect travel of a delivery driver in the dispensing chamber with a force equal to or greater than a force needed to push the fluid through a channel in communication with a treatment site, wherein the fluid provided in the fluid providing step is enclosed in a sac, the rotating step including the substep of rotating the first rotatable drive shaft to effect travel of the delivery driver in the dispensing chamber with a force equal to or greater than a force needed to break the sac.

24. A method, comprising the steps of:

providing a fluid in a dispensing chamber;

rotating a first rotatable drive shaft to effect travel of a delivery driver in the dispensing chamber with a force equal to or greater than a force needed to push the fluid through a channel in communication with a treatment site; and rotating a second rotatable drive shaft to effect travel of an anvil portion of a stapler relative to a staple driver of the stapler, the first rotatable drive shaft rotating step effecting travel of the staple driver relative to the anvil portion.

25. The method according to claim 24, wherein the first rotatable drive shaft rotating step includes the substep of effecting travel of a blade of the stapler relative to the anvil portion.

* * * * *

UNITED STATES PATENT AND TRADEMARK OFFICE
CERTIFICATE OF CORRECTION

PATENT NO. : 6,681,979 B2
DATED : January 27, 2004
INVENTOR(S) : Whitman

It is certified that error appears in the above-identified patent and that said Letters Patent is hereby corrected as shown below:

Column 1,
Line 10, after "6,488,197" insert -- , --; and

Column 10,
Line 13, replace "9" with -- 8 --;

Signed and Sealed this

Twenty-fifth Day of January, 2005

JON W. DUDAS
*Director of the United States Patent and Trademark Office*